United States Patent [19]

Haberzettl et al.

[11] Patent Number: 5,017,342

[45] Date of Patent: May 21, 1991

[54] DEVICE FOR IMMUNOASSAY DETERMINATIONS

[75] Inventors: Cecelia Haberzettl, Flemington, N.J.; Jack Geltosky, Doylestown, Pa.; Renée Perst, Lebanon, N.J.

[73] Assignee: Ortho Diagnostic Systems Inc., Raritan, N.J.

[21] Appl. No.: 201,515

[22] Filed: Jun. 1, 1988

[51] Int. Cl.$^5$ ............................................. B01L 3/00
[52] U.S. Cl. .................................. 422/102; 436/809; 436/810
[58] Field of Search ................ 436/535, 810, 809; 435/310, 299; 422/297, 301, 55, 58, 102, 99; 220/23.8; 294/7, 30, 55; 30/324, 141, 149, 325, 326, 327, 328

[56] References Cited

U.S. PATENT DOCUMENTS

| | | | |
|---|---|---|---|
| 3,219,421 | 11/1965 | Schwarz, Jr. et al. | 23/292 |
| 3,876,504 | 4/1975 | Koffler | 195/103.5 |
| 3,901,657 | 8/1975 | Lightfoot | 23/253 |
| 3,915,647 | 10/1975 | Wright | 23/253 |
| 3,932,141 | 1/1976 | Beall et al. | 422/99 |
| 3,938,961 | 2/1976 | Lanier | 422/102 |
| 4,210,418 | 7/1980 | Brown et al. | 23/230 |
| 4,230,664 | 10/1980 | Cais | 422/61 |
| 4,246,339 | 1/1981 | Cole et al. | 422/102 |
| 4,454,094 | 6/1984 | Bjorling et al. | 422/56 |
| 4,495,151 | 1/1985 | Ohyama et al. | 422/102 |
| 4,501,719 | 2/1985 | Williams | 422/99 |
| 4,510,119 | 4/1985 | Hevey | 422/71 |
| 4,591,556 | 5/1986 | Saxholm | 435/33 |
| 4,591,570 | 5/1986 | Chang | 436/518 |
| 4,596,774 | 6/1986 | Chang et al. | 435/68 |
| 4,599,315 | 7/1986 | Terasaki et al. | 422/99 |
| 4,628,036 | 12/1986 | Scheepens et al. | 436/520 |
| 4,675,299 | 6/1987 | Witty et al. | 436/165 |
| 4,681,782 | 7/1987 | Ozkan | 428/36 |
| 4,789,628 | 12/1988 | Nayak | 422/102 |
| 4,891,321 | 1/1990 | Hubscher | 422/99 |
| 4,956,150 | 9/1990 | Henry | 422/99 |

FOREIGN PATENT DOCUMENTS

0203443A2  5/1986  European Pat. Off. .

Primary Examiner—David L. Lacey
Assistant Examiner—Thomas E. Daley
Attorney, Agent, or Firm—Gale F. Matthews

[57] ABSTRACT

An assay device is provided which includes a support, generally planar and elongated in shape, upon which a biological binding reaction may take place. This assay support includes in its broadest aspect, three sections, a sample receiving well section at one end and a gripping section at the opposite end, with a connecting section therebetween. The sample receiving well section includes at least two spaced-apart receiving wells, generally at the end of the assay support, for the addition of binding reactants. Each of the wells has an open end on a first face of the support, a concave inner surface extending concavely into the support, and a convex outer surface which projects convexly from an opposed face of the support. These wells may serve as a depository to contain aliquots of binding reagents, as well as a sample under analysis, the sample under analysis possibly containing a substance that will bind to the binding reagents.

18 Claims, 4 Drawing Sheets

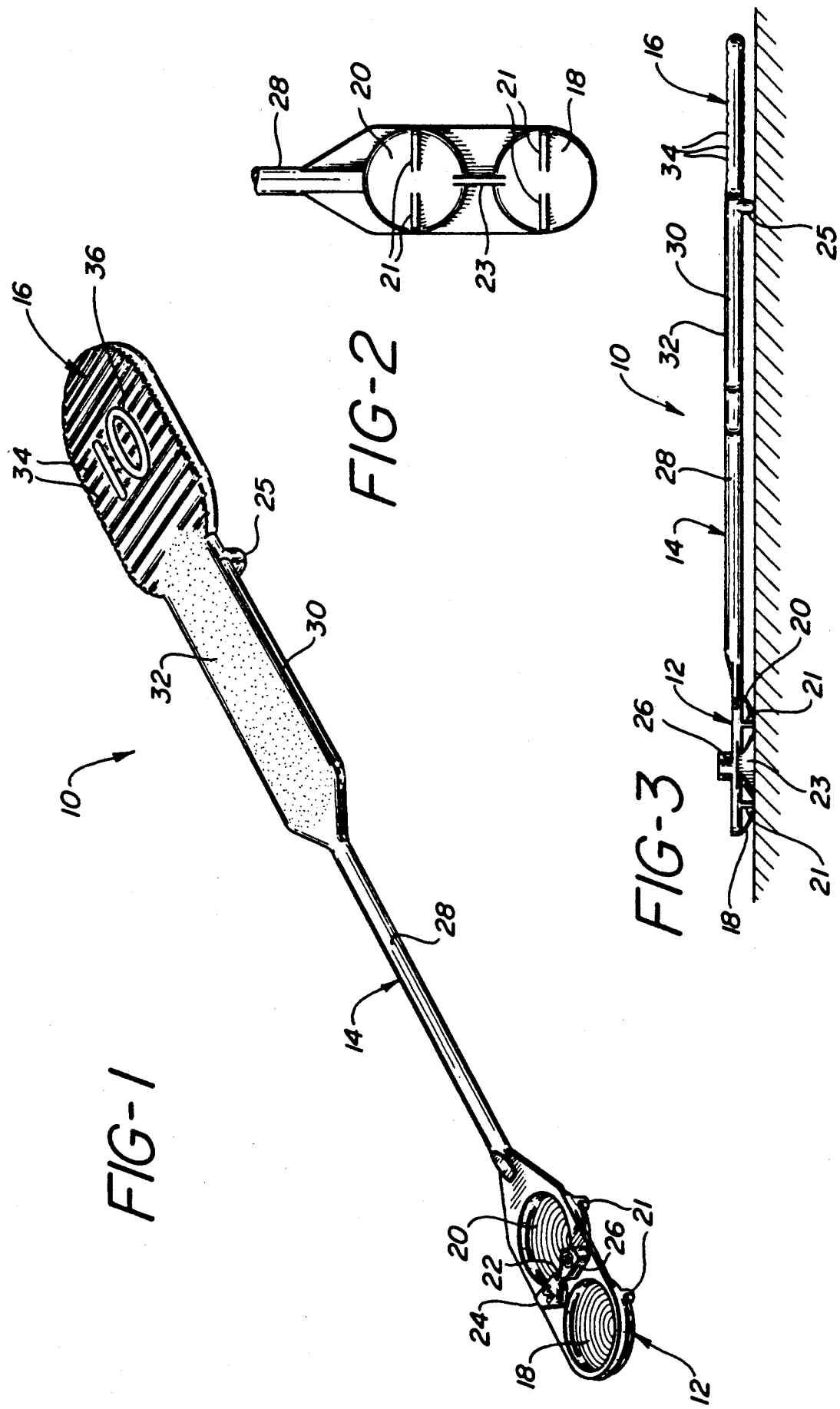

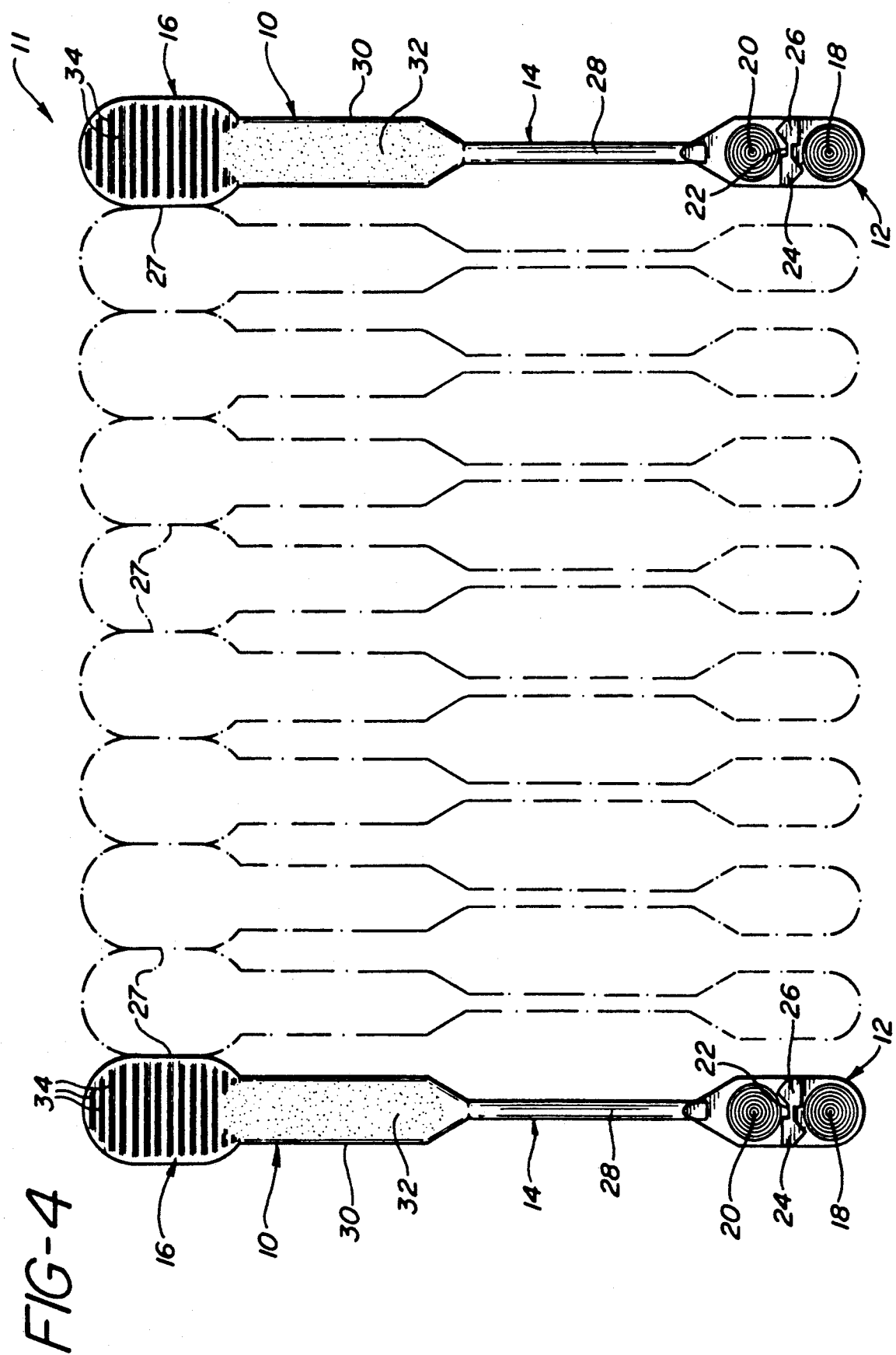

DEVICE FOR IMMUNOASSAY DETERMINATIONS

FIELD OF THE INVENTION

This invention is in the field of cell biology, virology, and immunology, and particularly relates to a novel immunoassay device and methods for the determination of substances in a sample under analysis, particularly antibodies.

BACKGROUND OF THE INVENTION

There has been described in the past numerous methods and materials for use in determining the presence of biological substances in a sample under analysis, particularly antigens and antibodies, and particularly when that sample is a human body fluid. One of the most commonly employed methods is an enzyme linked immunoabsorbent assay (ELISA). ELISA-type assays are often performed with the use of microtiter plates, which may be generally described as a plate molded out of a plastic or a similar material, having numerous wells for receiving aliquots of a sample and assay reagents. Microtiter plates are commonly employed in a clinical setting for the assaying of physiological fluid or excreta for the presence of a target analyte, which may often be an antibody or antigen. In fact, microtiter plates may even in some cases be purchased with antibodies already added to the wells, specific for the particular antigen under investigation. In preparing such precoated microtiter plates, individual aliquots of the antibody are either manually pipetted into each well to coat its bottom, or added to a series of the wells through automated pipetting techniques. Once in the laboratory setting, an aliquot of a sample under analysis is added to each well of the microtiter plate, usually by use of manual pipetting techniques. The sample is then allowed to interact with the antibody.

Frequently the number of individual wells in these microtiter plates can be very large. Repetitive pipetting, whether automated or manual leaves a large margin for error in the uniformity of coating of the antibody aliquots into each individual well. Non-uniformity of coating can introduce variability to the assay results, diminishing reliability of the assay and also affecting the overall sensitivity of the test.

Also, determinations utilizing ELISA-type technique generally demand a large amount of reagents which are oftentimes limited in supply because they are difficult or costly to obtain. Furthermore, the reaction time period necessary to carry out these types of assays practiced in the art, generally ranges about 2-4 hours.

SUMMARY OF THE INVENTION

In one aspect of the present invention, there is provided a device suitable for use in conducting biological assay determinations rapidly and efficiently with a comparatively small quantity of reagents, particularly immunoassay determinations. The presently claimed device provides the user with the flexibility of conducting such an assay with a chosen number, large or small, of samples. The assay may be performed without wasting a portion of the device, as is now the case when using a 90-well microtiter plate to run a much smaller number of samples.

The device essentially comprises a support upon which a biological binding reaction may take place, said assay support generally planar and elongated in shape. This assay support comprises in its broadest aspect, three sections, a sample receiving well section at one end and a gripping section at the opposite end, with a connecting section therebetween. The sample receiving well section comprises at least two spaced-apart receiving wells, generally at the end of the assay support, for the addition of binding reactants. Each of said wells has an open end on a first face of said support, a concave inner surface extending concavely into said support, and a convex outer surface which projects convexly from an opposed face of said support. These wells thus serve as a depository to contain aliquots of the binding reagents of the invention, as well as a sample under analysis, said sample under analysis possible containing a substance that will bond to the binding reagents, hereinafter termed "target analyte". The convex outer surface of at least one of the wells is also provided with at least one stabilizing leg adapted to preclude rotation of said wells when resting on a flat surface. The assay support of the invention is also provided with a leveling projection extending from said opposed face which is adapted to cooperate with said at least one stabilizing leg to maintain said support level when resting on a flat surface. The sample receiving well section of the device is also provided, in the space between said wells, and projecting from the first face of said assay support, with a dam means adapted to preclude the flow of a liquid sample from one of said wells to another.

The preferred assay supports of the invention are provided with two wells in said sample receiving well section in close proximity to one another, separated by the dam means. The dam means in this configuration comprises a labeling portion on either end which is essentially a raised block in the shape of an arrow, each block having a letter imprinted on it and pointing to a respective well. This preferred assay support is particularly useful for conducting comparative assays on a sample. The close proximity of the wells, one to another, along with the indicia labeling the contents of each well, and the dam means preventing contamination of the contents of one well by the contents the other, render this design particularly suitable for comparison studies.

The assay supports of the invention are provided singly or in a detachably connected planar series wherein they are joined to each other to form a plurality of assay supports, preferably ranging in number from about 2 to about 25, more preferably about 5 to about 15, most preferably about 5 to about 10. This planar series embodiment of the invention facilitates the conducting of an immunoassay with any desired number of sample numbers, as a desired number of supports may be easily detached from a series.

The assay supports of the invention, or the planar series containing two or more supports may be held manually or by mechanical means and dipped into a bath that contains a reagent, for the simultaneous coating of the reagent onto the sample receiving well section of each of the supports. The assay supports may thus be conveniently precoated with a desired reagent in a uniform manner, and used at a later time in a binding reaction.

In another aspect of the present invention, there is provided a method for biological assay determinations, using the device of the invention, especially in immunoassay determinations. In the preferred methods, comparison studies are conducted, such as the determination of IgG and IgM antibodies in human biological samples. The ratio of these last-mentioned antibodies provides a clinical correlation to past or present infection with Epstein-Barr virus, which among other things in responsible for mononucleosis infections. Using the preferred device as described herein, a color comparison can be made between the colors developed in each receiving well. A biological sample is added to the device, which has been pre-coated with antigen. If IgG or IgM antibodies are present in the sample, they will bind to the pre-coated antigen. Anti-IgM antibody is then added to a receiving well labeled with "M" and anti-IgG antibody is added to the receiving well next to it, that is labeled with "G". Substrate is added to both wells and color develops if the respective antibodies are present. The user then compares colors produced in one well versus the other to derive an appropriate relative ratio of one antibody to the other.

The device and methods described herein provide several advantages. The invention represents a major simplification of existing immunochemical methodology and devices, in that the claimed assay support configuration eliminates well to well variability of the amount of a first binding reactant coated into each of the wells of the support, to which samples, possibly containing target analyte would then be added for a binding reaction. Reproducibility of such coatings have been a problem for the microtiter plates commonly used in this art, wherein the first binding reactant is pipetted into the well. The present construction allows one or more of the supports to be dipped, all at the same time, into the first binding reactant, precoating the support for future assay determinations. p The invention also eliminates the need for a substantial incubation time period to allow the binding reaction to occur between a possible target analyte and the first binding reactant, or any additional binding reactants. The particular construction of the device as will be described in detail herein, allows a good dispersion of reactants, and also allows binding reactions to take place in a small, easily monitored area. The concentration of the first binding reactant precoating material can be greatly increased, since the area this coating is to cover is relatively small, but has the advantage of good dispersion capability, thereby greatly reducing the incubation time necessary to allow binding events to occur.

BRIEF DESCRIPTION OF THE DRAWINGS

FIG. 1 is a perspective view of a preferred embodiment of the assay device of the invention.

FIG. 2 is a rear elevational view of the receiving well section of the assay support of FIG. 1.

FIG. 3 is a side elevational view of the preferred assay support of FIG. 1, as it rests levely on a flat surface.

FIG. 4 is a plurality of the assay supports shown in a series, wherein the supports are detachably joined to one another.

DETAILED DESCRIPTION OF THE INVENTION

Figure 5:
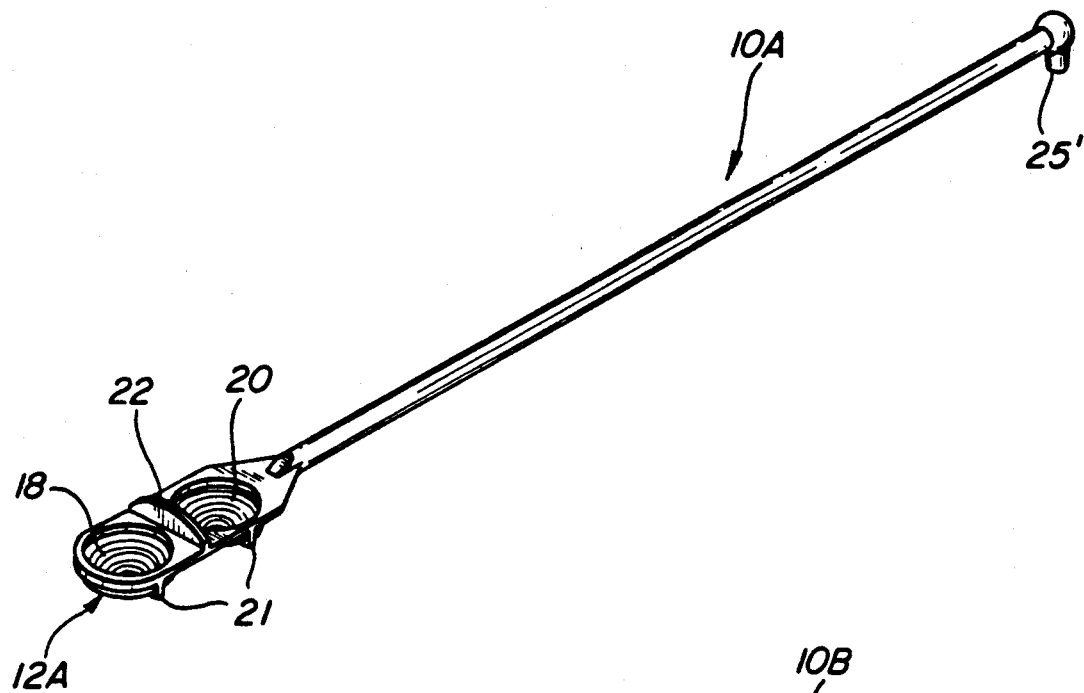
FIGS. 5, 6 and 7 depict alternate embodiments of the assay support of the invention.

The assay device of the invention comprises a support for a biological assay, generally planar and elongate in shape, said support comprising a gripping section, a sample receiving well section, and a connecting section therebetween, each of said sections being aligned along a longitudinal axis. The sample receiving well section is generally at one end of said support, and comprises at least two receiving wells to act as depositories for the reactants of an assay, particularly an immunoassay. Each of said wells has an open end on a first face of said support, a concave inner surface extending concavely into said support, and a convex outer surface which projects convexly from an opposed face of said support. The depth and diameter of the receiving wells in said receiving well section may vary widely, however it is preferred that they be of a sufficient size to contain at least about 10 microliters of liquid medium containing reactants for the assay.

Each well is also separated from an adjoining well with a dam means to prevent diffusion of the contents of one well into the other. The dam projects from the first face of said support in an area between adjacent wells and preferably extends transverse to the line between the centers of said adjacent wells. The dam may take on any form to serve this purpose. It is discovered however, that the height to which the dam extends from the first surface should vary regularly along the length of such extension, i.e., should increase from either end toward the center of such length or, preferably be of uniform height across such length. Should the dam means have an irregular height across such length, i.e. increasing and decreasing and then increasing again, such variation will create capillary action between the walls of the dam and allow liquid deposited in the well to rise to the highest level of the dam and leak across the lower levels into the adjacent well, thus, contaminating such well.

The receiving well section of the assay support is of an area appropriate to contain the desired number of receiving wells. It should be appreciated that the dimensions of the receiving well section will vary with the number of receiving wells contained therein, their positioning relative to one another, and the dimensions of the wells themselves. In the preferred embodiments, the receiving well section is approximately 30 mm in length, 22 mm in width, and 31 mm in its greatest depth, with the well diameter of the receiving wells themselves being approximately 10 mm. The size of the entire receiving well section in the preferred embodiments is optimized to require the smallest amount of a first binding reactant precoating solution, when it is desired to precoat the receiving well section of the device.

The receiving wells are further provided with a structure on the convex surface thereof to allow the device to sit stably on a flat surface, so as not to tip the contents that would be added to the wells. In the preferred embodiments, the convex surface of the wells are provided with two structures each, that serve to square off the rounded shape, termed stabilizing legs.

In the particularly preferred embodiments, the concave surface of the receiving wells are roughened or otherwise provided with a series of ridges in a manner that serves to increase the surface area of the well during the first binding reagent coating process, and also to facilitate dispersion of all the reagents eventually added to the coated wells, to aid in the overall binding reaction. It should be appreciated that aliquots of reactants contained in a liquid medium tend to "bead-up" when added to certain substrates, such as plastic substrates. It has been discovered that reactants contained in a liquid medium will disperse better with the aid of this roughening, thus enabling the binding reaction to take place in a small area. This also allows the binding reaction to take place with the use of small amounts of reactants in a liquid medium, preferably amounts as small as about 10 microliters to about 100 microliters, Any type of roughening in a configuration that will accomplish this end may be suitably used, however, in the preferred embodiments, ridges are provided, particularly in the form of concentric circles on the concave surface of the wells. These ridges may be conveniently provided during formation of the device itself from molten plastic.

The receiving well section may have a labeling portion contiguous with or even a part of the dam means, e.g. on the top of the dam means. This labeling portion may have indicia upon it to make confusion of samples in carrying out the assay techniques less likely to occur. For example, the fist letter of the name of a particular reactant may be provided next to the well to which that reactant should be added. Conventional molding, stamping or imprinting techniques may be used for this purpose. In assay support configurations wherein there is little room for a letter to be provided of a size that may be easily visualized, a raised block may be positioned contiguous with the dam means and next to a well, with a letter thereupon. The raised block could also be in the shape of an arrow pointing to the appropriate well to which the user would add a particular reagent. This feature is present in the preferred assay supports of the invention.

The connecting section of the assay support is contiguous with the receiving well section, and to that end generally tapers substantially from the receiving well section, and connects said section with the gripping section. The connecting section may be of any suitable shape, rounded or flat, or a combination of both. This section may be of any suitable length to enable the device as a whole to be easily held during any precoating process, and then placed on a flat surface to conduct a biological binding assay therewith.

In the preferred embodiments, at least a portion of the connecting section is provided in a flat configuration to enable labeling of the device, such as is commonly needed in a clinical or research setting when it is useful to keep track of many different samples being assayed. The labeling region of this connecting section is often roughened so that the user can easily write thereupon, any required information. It should also be appreciated that the assay support could also be provided as prenumbered in this labeling region for ease in user recognition when conducting a series of samples in an assay.

The gripping section of the device is contiguous with the aforementioned connecting section and forms a terminal portion of the device. In the preferred embodiments, the gripping section is of a configuration that easily lends itself to a manual or mechanical holding of the device for a desired precoating process, or for user facility when conducting an assay. Thus, in the preferred embodiments, the gripping section is ridged, or in some other way roughened, so that it will not slip from the user's grasp very readily. It may also be provided with large easy to visualize numbers for sample or patient identification purposes.

To enable that the device sit levelly on a flat surface across its entirety, a separate structure is provided at one or more places along the connecting section or gripping section, such structure termed a leveling projection. The leveling projection is of a size and height that will allow this portion of the device to sit on a flat surface in a manner that compensates for the depth of the receiving wells in the receiving well section of the device. This structure obviates spilling and nondispersion problems inherent in conducting an assay with a device sitting on an incline.

In the most preferred embodiments of the invention, the individual assay supports are detachably connected to one another, substantially in a single plane, so as to provide a planar series of assay supports. This planar series configuration is particularly useful to the user for assay determinations with more than one sample. It is within the contemplation of the invention that any reasonable number of assay supports may be connected to one another and thus provided in a series. In the preferred embodiments, the number in any one series is usually between about 5-15 individual assay supports. In the most preferred embodiments the assay supports are juxtapositioned next to one another and connected by bonding along the length of the gripping section. The bonding is achieved during a molding process, with a bond that may be easily broken by mechanical manipulation, but does not break spontaneously, such as during shipment of the series, or when the device is placed on a lab bench and the like. The breakable bond enables the user to break off however many assay supports are needed in a given assay. For example, if it is desired to assay 15 samples, an assay support series of ten may be used in its entirety, along with half of a second series of ten, totaling 15.

In the preferred embodiments, when the assay support device is provided in a planar series, there is also provided a spacer projection extending from the sample receiving well section of the opposed face, in such a manner that it is adapted to cooperate with the dam means of an adjacent planar series. The presence of this spacer projection keeps each support in a planar series separated from one another for coating of the series when a number of them are held in tandom by mechanical means. If each support in a series is not adequately separated from another during coating, they may touch at various points, thereby affecting the uniformity of the coating of the receiving well section. In the preferred embodiments, the height of the spacer projection is of a height necessary to maintain, in cooperation with the dam means of an adjacent planar series, at least about 2.0 mm between one series and said adjacent series. In the preferred embodiments this height is usually about 1.0 mm to about 1.22 mm. Greater than about 1.5 mm tends to allow one series to fan out from the adjacent series when being held by mechanical means, so that fewer series can be held in any one coating process, thereby decreasing the economics of such a coating process.

The following is a more particular description of the preferred embodiments of the assay support device of the invention as illustrated in the accompanying figures, in which like reference characters refer to the same parts throughout different views or in alternate embodiments. The drawings are not necessarily to scale, emphasis instead being placed upon illustrating the principles of the assay device, as well as providing representative examples.

Referring now to FIGS. 1 and 2, which are perspective and rear elevation views respectively, of a single assay support device 10, the device is comprised of three sections, a sample receiving well section 12, a connecting section 14, and a gripping section 16. The sample receiving well section 12 depicted therein has two receiving wells 18 and 20 separated by a dam means 22. The dam means 22 also comprises triangular labeling portions 24 and 26, the apex of the triangular labeling portion pointing to each respective receiving well. Labeling portion 24 is marked with an "M" which is a symbol to represent IgM, an antibody present when there is an active disease state of mononucleosis. Labeling portion 26 is marked with a "G" which represents IgG and points to the receiving well contiguous with the connecting section of the device.

The sample receiving well section 12 tapers to connecting section 14 which comprises a cylindrical portion 28, adjoining the tapered portion of the receiving well section. The cylindrical portion 28 of the connecting section is contiguous with a flat labeling region 30 suitable for the placement of labels or for the writing of information thereupon. Labeling region 30 has a roughened surface 32 for adherence of an appropriate label. The labeling region 30 adjoins the gripping section 16, having ridges 34 for ease in manual or mechanical grasping. Gripping section 16 also has numeral 36 provided thereon for easy numerical identification of a sample.

The convex surface of receiving wells 18 and 20 have stabilizing legs 21 which act as legs to preclude the receiving well section of the device from rotating when sitting evenly on a flat surface. Legs 21 also serve to strengthen the receiving wells. Spacer projection 23 is positioned between the convex surface of receiving wells 18 and 20 and serves, as will be described herein in greater detail, to space one assay support device from another juxtapositioned tandemly to the rear of it during a mechanized dipping process for coating of a desired first binding reactant onto the device. Labeling region 30 is provided with a company insignia (not shown), and is separated from the gripping section 16 by a leveling projection 25 which cooperates with stabilizing legs 21 to allow the assay support device to sit levelly on a flat surface along the entire length of the device. FIG. 3, a side elevational view of the device 10, demonstrates the manner in which the device sits on a flat surface.

FIG. 4 shows another preferred embodiment, a planar series 11 of assay supports joined to each other at bond 27 which can be broken with manual manipulation, to separate each individual support in the series, so that any desired number of supports may be used to conduct an assay.

FIG. 5 is an alternate embodiment, 10A, of the device of the invention having dam means 22 tapering at either end between the two receiving wells 18 and 20, in the receiving well section 12A. There is no labeling for the receiving wells, nor for the terminal portion of the device. Leveling projection is a small knob 25' at the end of the terminal portion of the device.

Figure 6:
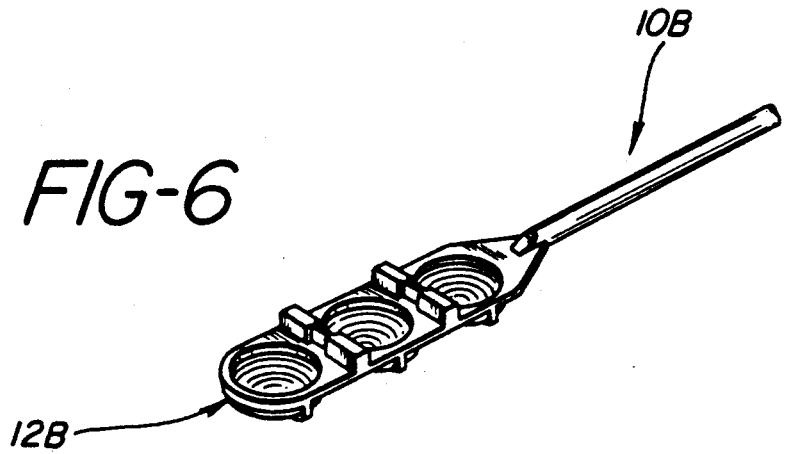

FIG. 6 is yet another embodiment, 10B, of the invention, with sample receiving well section 12B having three receiving wells instead of two as shown for the preferred embodiment.

Figure 7:
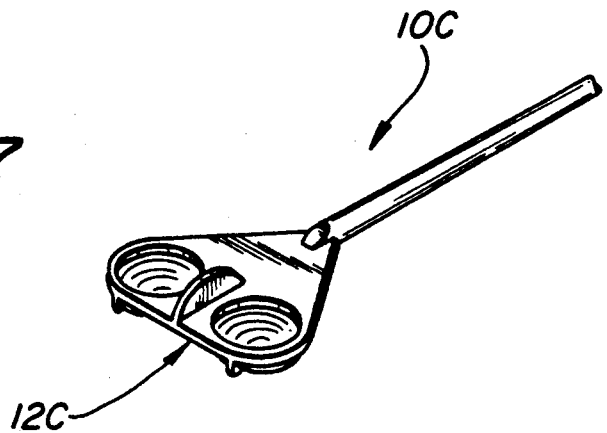

FIG. 7 is an alternate embodiment, 10C, with sample receiving well section 12C having two wells disposed transversely.

Figure 8:
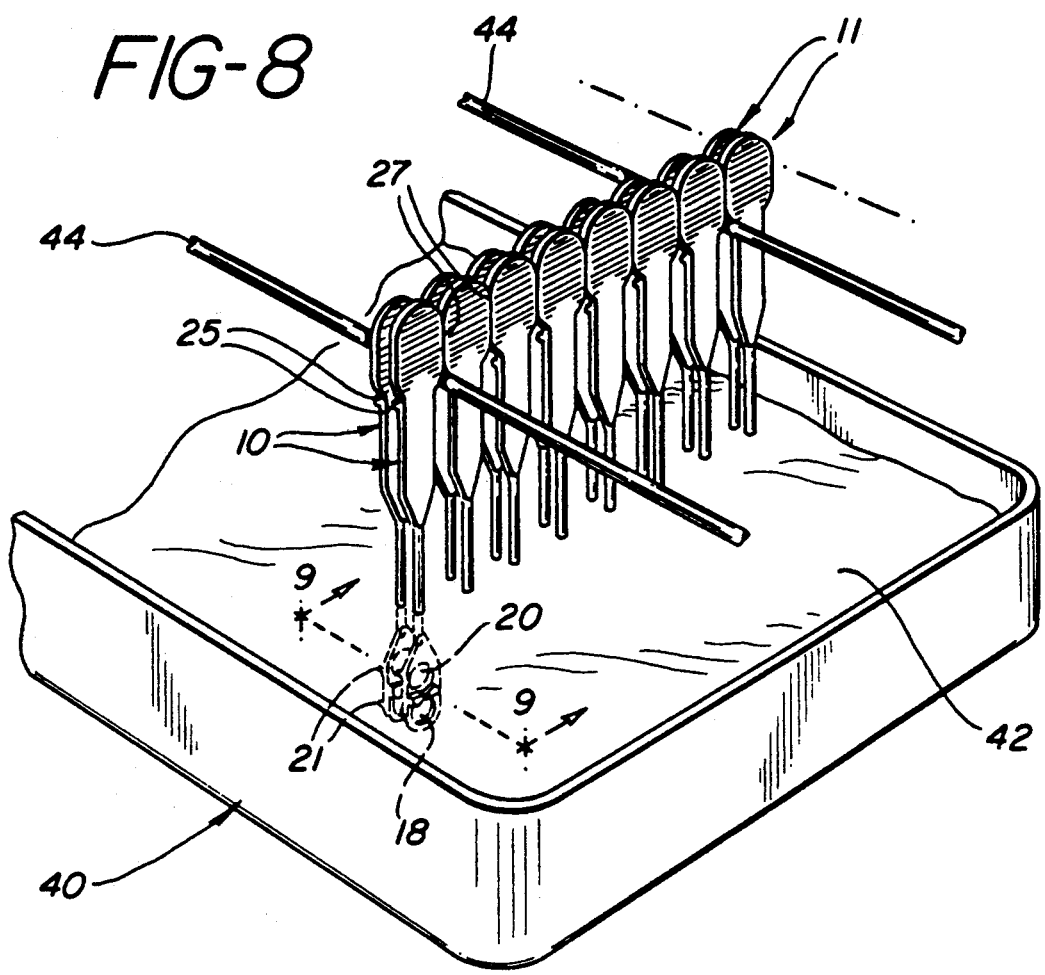
FIG. 8 is a perspective view showing one embodiment for the pre-coating of a planar series by vertical dipping into a bath that contains a coating reagent.

FIG. 8 shows a bath 40 with a coating solution 42 and dipping support rods 44, from which are suspended two planar series 11 of assay supports, representative of a planar series undergoing a precoating process. For purposes of illustration, only eight assay supports have been shown connected to one another. It should be noted that any number of detachably connected assay supports may be connected to one another and suspended for coating purposes.

Figure 9:
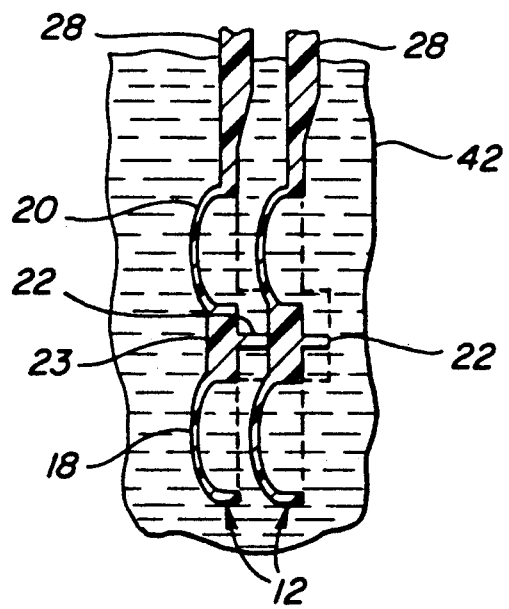
FIG. 9 is a cross-sectional view taken along line 9—9 of FIG. 8.

FIG. 9 shows how the sample receiving well sections 12, when hanging from the dipping support rods 44, maintain a substantially parallel relationship, so as to permit uniform coating of this section with the coating solution 42 contained in bath 40. This is accomplished by the cooperation of dam means 22 of the assay supports in one planar series 11 with spacer projection 23 of the assay supports in an adjacent planar series.

The primary function of the assay support of the invention is to act as a site or focus for a biological binding reaction, particularly an immunoreaction. In this regard, it is particularly preferred that the device be pre-coated with a first binding reactant, to which target analyte may be added, together with additional reactants, if need be. First binding reactants within the contemplation of the invention are protein in nature. To this end then, the composition of the assay support device of the invention may be of any conventional composition to which protein will adhere. For example, many plastics are conventionally available and suitable for this purpose, and thus the entire device can be easily molded into desired shapes using conventional molding techniques. A wide variety of organic and inorganic polymers both natural and synthetic may be employed, including polyethylene, polyvinyl chloride, polypropylene, poly-4-methylbutene, polystyrene, polymethacrylate, polyethylene terephthalate, rayon, nylon, polyvinyl butyrate, polyformaldehyde, cellulose, cellulose acetate, nitrocellulose, etc. Other materials which may be considered include paper, glass, fiberglass, ceramics, metals metal foils, metalloids, semi-conductive materials, and others. In the preferred embodiments, materials generally used include nylon and high impact polystyrene, the latter being the composition of choice.

The assay support formed from the aforementioned materials will typically be of a thickness of about 0.7 mm to about 0.8 mm. The composition can be opaque, translucent, or transparent, however, the signal generated during an assay should not be masked by the nature of the composition used in forming the support. In the preferred embodiments, the composition is opaque and of a color that may vary widely. When color visualization is an integral part of the assay, the device should be a color to offset the color that may develop as a result of signaling of the biological binding reaction. For example, a solid white has often been useful for facilitating detection of faint colors, for example faint greens, yellows, blues, and the like developed during binding reactions. In the preferred embodiments, the device is a solid white color which can be obtained by the addition of a talc or titanium dioxide or the like to the plastic during the molding process. However, one skilled in the art will appreciate that many other colors may be more suitable depending on the particular reaction it is desired to carry out with the assay device of the invention, and the ensuing color visualization.

The novel configuration of the devices of the invention allow the receiving wells themselves to be conveniently dip-coated or otherwise pre-coated with a first binding reactant. In pre-coating the assay support devices of the invention with a selected first binding reactant, several parameters need be considered. When the assay support device of the invention, whether a single support or a series, is dipped into the coating solution, containing such first binding reactant, care should be taken that the individual paddle supports do not touch one another or the sides of a vessel holding the appropriate pre-coating solution. This will help to insure that the coating is uniform.

One advantage to the series configuration of the assay support device as illustrated in FIGS. 4, 8 and 9 is that a number of these series may be held by a mechanical means in a controlled manner wherein the sides of the series do not touch the walls of the container holding the pre-coating solution, and each series is sufficiently spaced from any neighboring series. The level of coating solution utilized for this coating process, termed dip-coating, should be sufficient to cover the entire receiving well section of the assay support device. The receiving well section may be also pre-coated by any other conventional technique, such as for example, the spraying of said devices with a coating solution.

Another advantage of the configuration of the device of the invention, is that the distance between receiving wells may be kept at a minimum. Therefore, the volume of a dipping solution in a dipping bath may also be kept at a minimum, which might curtail the use of costly components. One skilled in the art will also understand that vessels containing the substance desired to be coated onto the assay devices of the invention should be fabricated from materials that are not amenable to binding protein, so that the first binding reactant, a protein, will preferentially bind to the assay support device and not remain behind in the coating vessel, coating the sides of the vessel.

As described herein, the first binding reactant is generally protein in nature, particularly one or more peptides. A wide variety of natural proteins or protein sub-units may be pre-coated onto the device. Such proteins include histones, nucleoproteins, lipoproteins, glycoproteins, somatotropin, prolactin, enzymes, human plasma protein constituents, including human albumen, thyroxin binding globulin, haptoglobin, ceruloplasmin, myoglobin, fibrinogen, plasminogen, poly and monoclonal immunoglobulins of the A, D, E, G or M classes, free light or heavy chains of immunoglobulins, an F(ab) fragment or an F(ab)$_2$ fragment, variable regions, hypervariable regions, or constant regions of the immunoglobulin; complement factors, blood clotting factors, peptide and protein hormones including insulin, glucagon, erythropoietin, FSH, LH, TSH, HCG, oxytocin, vasopressin, and the like. If it is desired to precoat with an antibody, poly and monoclonal immunoglobulins of the A, D, G, or M classes, or free light or heavy chains of the immunoglobulins can be prepared in well known polyclonal and monoclonal antibody techniques. Polyclonal antibodies can be raised in a variety of test animals including mice, rats, goats, rabbits, horses and others. Monoclonal antibodies can be prepared using well-known techniques such as that disclosed by Kohler and Millstein, "Continuous Cultures of Fused Cell Secreting Antibody of Predetermined Specificity", *Nature*, Volume 256, pages 495–497, Aug. 7, 1975.

As is conventional to this art, an overcoating process should also be performed to insure that all the sites on the assay support itself are bound, so as to avoid nonspecific binding of any target analyte present in the sample under analysis during the performance of the assay. Conventional overcoating proteins may be used, including albumin, goat serum, horse serum, rabbit serum, gelatin and fetal calf serum. Preferred for use herein are goat serum and fetal calf serum.

Additionally, the stability of the binding reactant coating may be increased by the addition of components to the overcoating that serve to keep the assay supports "wet". While the use of overcoating techniques in general are not new to the art, the present inventors have discovered that it is essential to keep the assay supports of the invention wet during any ensuing packaging and storage time period. This is contrary to that which is normally accepted in the art. For example, microtiter plates historically have been actually packaged in aluminum foil with a desicating agent to keep the plates (with a binding substance bound thereon) as dry as possible. The present inventors have discovered that the stability of the first binding reactant coated onto the assay supports actually improves tremendously with the addition of a syrupy alcohol or sugar to the overcoating solution. Of the compounds suitable in this regard, may be mentioned sucrose, trehalose, and glycerol. In the preferred embodiments of the invention, glycerol is the compound of choice for use in the overcoating solution to maintain this wet condition of the supports during a storage period. Concentrations of greater than about 5% are preferred, more preferred being about 10% to about 50%, most preferred being about 10% to about 25%.

IMMUNOASSAY TECHNIQUES UTILIZING THE DEVICE OF THE INVENTION

The assay support device of the present invention, pre-coated with a first binding reactant as described above, is particularly suited for use in conducting immunoassay techniques with a biological sample under analysis, said sample possibly containing target analyte. It will be understood by those skilled in the art that a labeling or indicating means is necessary in such an immunoassay system, to signal the presence of an immunoreaction between the binding reactant coated on the device and the target analyte present in the sample. Typical indicating means include radioisotopes such as $^{125}$I $^{131}$I, enzymes such as alkaline phosphatase, horseradish peroxidase, beta-D-galactosadase and glucose oxidase, and fluorochrome dyes such as fluorescein, rhodamine and phycobiliproteins. In the preferred assays, this indicating means is a compound that is generally linked to a separate molecule such as to a second antibody that will bind to the immunoreaction product. The present invention is not restricted to a specific means of detection or a specific type of label. However, this indicating means preferably employs an enzyme label and therefore, the assay may be properly called an ELISA or an EIA. Enzymes that may be useful in this context include beta-D galactosidase, glucose oxidase, beta-D-glucuronidase, lactate dehydrogenase, lactoperoxidase, alkaline phosphatase and horseradish peroxidase. Horseradish peroxidase, glucose oxidase and alkaline phosphatase are the enzymes of choice in the assay of the invention. One skilled in the art will also readily understand that any substrate such enzymes are capable of acting on to produce a color signal will be suitable for use in conjunction therewith.

In the preferred embodiments of the invention, the indicating means is an enzyme linked to a separate molecule such as to a second antibody, forming a conjugate that will react with the immunoreaction product. Together, the indicating means linked to this second molecule forms the second binding reagent of the method of the invention, termed a "labeling reagent". Preparation of this labeling reagent may be accomplished using any conventional technique. For example, an enzyme label is often commercially available with an active group that will react with a protein. Often the active group is activated carbonyl including nitrogen and sulfur analogs, illustrated by carbocyclic acids activated with carbodiimide, carbonate monoester, in a mixed anhydride, carbonyl chloride, and active ester. Illustrative of these are N-hydroxy, succinamide, paranitrophenyl, isocyanate, isothiocyanate, imidate ester, thioester, thionoester, and others. Reductive alkalation, active halogenation, and other well-known techniques can be used. Often antibodies pre-labeled with enzymes are even available commercially.

The present inventors have discovered that the concentration of this labeling reagent can be critical in the performance of the assay of the invention, and that very high concentrations can significantly decrease the amount of time necessary to detect the immunoreaction product. This detection time conventionally ranges from 2–4 hours, and may be decreased to an amount of a few minutes by the use of the device and assay technique of the invention.

The steps of a typical immunoassay are next described. In the first step in the performance of an immunoassay, an aliquot of a biological sample, possibly containing target analyte that will bind to the pre-coated first binding reactant, is added to the receiving wells of the claimed device, using any suitable dispensing means such as a pipette, dropper, and the like. It is preferred that the dispensing means utilized will dispense uniform aliquots to each well. The biological sample is in a liquid medium and may or may not be subjected to conventional purification techniques prior to testing. For example, if the sample assayed is blood, it may be desirable to assay blood serum or plasma as opposed to whole blood, to rid the sample of interferents.

The immunoreactants are allowed to incubate for a time sufficient to allow target analyte to bind to the first binding reactant coated in the wells. Excess unbound target analyte in the biological sample is then washed from the immunoreaction with any conventional washing solution that will not interfere with the binding event or allow non-specific binding, or in any other way skew the results of the test. In this regard then, distilled water, saline, phosphate buffer, methylcellulose, polyoxyethylene sorbitan monolauryl ether, such as Tween 20 ™, manufactured by Kao-Atlas Co. Ltd, and the like, in any combination, may be used as a washing solution.

To the immunoreacted product in each receiving well of the device is then added a second binding reagent, the labeling reagent. This mixture is allowed to incubate for a time sufficient to allow the labeling reagent to bind to the immunoreacted product. In the preferred embodiments, at least about two minutes is allowed for this incubation. A second washing step is then employed to remove unreacted labeling reagent. When this labeling reagent utilizes an enzyme detection system, an appropriate substrate is then added in a next step, in conventionally dictated amounts, to signal the presence of the immunoreacted product. In the preferred embodiments, a critical incubation time period of about 90 seconds to about 150 seconds, preferably about 110 seconds to about 130 seconds, have been employed to carry out this assay step. Detection of the label in the receiving well of the device may be accomplished through color visualization with the unaided eye, or through the use of any necessary instrumentation to detect the presence of the label. Detection of the label in the receiving well may be qualitative only, giving a yes or no answer as to whether or not there is the presence of immunoreacted product. Alternatively, quantitative detection may be had by comparison of colors or instrumentation values to standard reference values, such as standard concentration curves and the like, techniques generally accepted in the art. Comparisons of the colors or color intensity developed in one well versus the other also may serve as an indication of relative amounts of two or more immunoreactants, in those cases wherein different labeling reagents are used.

DETAILED DESCRIPTION OF THE PREFERRED DEVICE AND IMMUNOASSAY USING SAME

The assay support device of the invention is particularly suited for use in the detection of the Epstein-Barr virus (EBV), a member of the herpes virus family, causative of infectious mononucleosis in humans. EBV is an extremely common environmental agent infecting 80–100% of the individuals around the world. The initial or primary infection may be acute or sub-clinical. This is followed by a long period during which the EBV infection is latent in B lymphocytes present in the circulating blood, lymph nodes and spleen.

The presence of an immunoglobulin, termed IgM immunoglobulin, in a person's blood is a general indication that they have an acute case of mononucleosis or that they are just recovering from mononucleosis. The presence of an immunoglobulin termed IgG immunoglobulin in a person's blood indicates that the person had mononucleosis in the past or is recovering from it. In those cases where both immunoglobulins are present, if IgG is greater than IgM, this is an indication that the infection is a past infection. If the opposite is true, then the infection is acute and active. If the concentration of IgM is equal to that of the IgG, this is an indication that the disease is also acute, but that the person is starting to recover. If one were able to distinguish the relative ratios of these immunoglobulins, a key diagnostic advantage would be offered in that a patient may be diagnosed as having an acute or past infection of mononucleosis. Thus, if a patient's blood sample tests as having a past infection, and yet the clinical symptoms are consistent with mononucleosis, an attending physician would realize that these symptoms must be attributed to some other cause. It should also be appreciated that a patient who is ready to "seroconvert", i.e. convert from one type of immunoglobulin to another, would have almost an equivalent concentration of each antibody.

The presently claimed device and method of immunoassay is particularly suited for detecting the presence of IgG or IgM and comparing their relative amounts in a biological sample, most preferably in blood serum or plasma samples. An illustrative diagnostic system in kit form embodying the preferred aspect of the present invention comprises the assay support device of the invention in a series format. The series is first precoated with an antigen or fragment thereof of the Epstein-Barr virus, that will immunoreact with antibody that might be present in a patients' blood. The whole protein may be used, however, background reaction may be minimized if a particular antigenic sequence is used.

Classicly, the primary infection is detected by antibody to the viral capsid antigen (VCA) and the convalescent phase is noted by the rise of antibodies to the EBV-encoded nuclear antigens [EBNA] [Henle et al., *Hum Pathol.*, 5:551–565 (1974)]. EBNA-1, (also sometimes referred to herein as EBNA), the first nuclear antigen to be recognized, has been identified as a 65,000 to 85,000 kilodalton (kD) protein by the immunoblotting technique [Strnad et al., *J. Virol.*, 38:990 (1981); Hennessey et al., *Proc. Natl. Acad. Sci. USA.* 80:5665–5669 (1983); and Billings et al., *Proc. Natl. Acad. Sci. USA*, 80:7104 (1983).

Synthetic peptides containing portions of the glycine-alanine EBNA-1 region have been shown to be reactive with sera from patients with EBV-IM [Rhodes et al., in *Herpes virus*, R. Rapp ed., Alan R. Liss, New York; p. 487–496 (1984); Rhodes et al., *J. Immunology*, 134:211–216 (1985); Smith et al. *J. Infec. Dis.*, 154:885–889 (1986) and Geltosky et al. *J. Clin. Lab Analysis*, 1:153–162 (1987)]. As shown in U.S. Pat. No. 4,654,419 and subsequently elsewhere, the peptide denominated P62 can be used in an ELISA assay to distinguish serologically, the acute phase of EBV-IM from the convalescent phase and recovery phase of IM [Smith et al. *J. Infec. Dis.*, 154:885–889 (1986) and Geltosky et al. *J. Clin. Lab Analysis*, 1:153–162 (1987)]. This antigenic sequence correlates well with the disease symptoms, and thus is preferred herein as the first binding reactant coated onto the receiving wells of the device.

The acute phase of the disease is detectable by the appearance of IgM antibodies to this peptide. During the convalescent phase, the IgM antibody titre falls and IgG antibody can be detected [Smith et al. *J. Infec. Dis.*, 154:885–889 (1986)]. Patients with a long past infection have IgG antibodies to the peptide as the predominant immunoglobulin class.

Thus, in the particular preferred embodiments, a polypeptide such as polypeptide P62 is used as an antigen, and is affixed to the receiving wells of the assay support device by a dip-coating process. A planar series of devices is held either manually or by a mechanical means and dipped into a solution containing approximately 8 mg/L to about 20 mg/L, preferably 8 mg/L to about 12 mg/L, and more preferably 9 mg/L to about 10 mg/L of the antigen in a medium such as a buffer with slightly alkaline pH, for example, borate buffer. This antigen coating solution is held in a vessel that is made of material that will not encourage the non-specific binding of the coating antigen, preferably stainless steel. This series is passed through the solution so that the antigen will become coated onto the receiving well section. Non-specific binding sites on the assay supports are thereafter typically blocked with an overcoating of a protein that does not include a sequence to which anti-Epstein-Barr virus antibodies would bind or immunoreact, examples of which are bovine serum albumin, goat serum, calf serum, rabbit serum, and fetal calf serum. The preferred overcoating protein in this regard is fetal calf serum. Parameters such as the length of time of the coating process, the temperature at which the coating process is conducted, the liquid media, such as buffers used, and the concentrations of the coating protein and the overcoating protein may all be routinely optimized by one skilled in the art.

The preferred diagnostic system of the invention in the kit form also includes separately packaged anti-human IgG and IgM antibodies, each linked to an enzyme such as horseradish peroxidase, as the label or indicating means. For the convenience of the end user, and to lessen the likelihood of confusing these reagents, the anti-IgG conjugate (ie: the anti-IgG antibody conjugated to label, such as horseradish peroxidase) is typically colored green with a stable dye that will not precipitate, change color, or the like when added to the reagent. FD & C dyes may be used for this purpose. The anti-IgM conjugate is typically colored red, also with a FD&C dye, as it has been discovered that other red dyes might not be stable in the system. The anti-IgG and anti-IgM antibodies may generally be provided as polyclonal or monoclonal antibodies and then linked to the horseradish peroxidase or a similar label by conventional means such as by heterobifunctional coupling procedures.

One skilled in the art will appreciate that stability of the labeling reagent conjugate as described herein is dependent to some extent on the diluent media it is contained in, specifically with regard to the ionic strength, the pH, and the type of buffer used. Although some conjugates are stable in buffer alone, others must be stabilized through the use of a protein or other component such as potassium ferricyanide, glycerol, gelatin, and the like. The greater the stability of the reagent, the longer the shelf-life of that reagent in its diluent form. Stability is not as big a problem if the user has the luxury of storing the reagent as a concentrate, and then dilutes it prior to use in an immunoassay. Preferred components used to enhance the stability of the reagent as described herein are fetal calf serum, phosphate buffer, thimersal, and potassium ferricyanide, particularly fetal calf serum and potassium ferricyanide in combination.

Within the context of the presently claimed assay, it has been discovered that the concentration of the labeling reagents (the IgG and the IgM conjugates) is critical to achieving an accurate analysis of the ratio of IgG to IgM, present in a sample under analysis, especially within the very short incubation times utilized.

High concentrations of antibodies in a relatively small amount of reaction medium serves to reduce the incubation time for detecting the presence of the immunoreaction product to a period of a few minutes, as opposed to the conventional few hours. However, any unmonitored excess of one or the other conjugate will disturb the delicate balance between the detection of the IgM and the IgG in the sample, and will bias the relative comparison of these antibodies present in the sample. Further, antibodies differ from one another in their binding affinities. Thus, one antibody conjugate may bind to target antibody immobilized to antigen faster that the other conjugate within a given time period. Accordingly, in the preferred embodiments, the binding of the anti-IgG and anti-IgM are normalized, with respect to a two minute incubation period, by adjusting the concentrations of each conjugate, so that each one binds in a predetermined ratio within this period. To achieve this, various concentrations of a given conjugate may be compared to a standard conjugate at a predetermined concentration that develops a certain color intensity upon binding to the target antibody. A suitable concentration of that respective conjugate is one that will develop that same color intensity upon binding of the conjugate to that same predetermined concentration of target antibody. Once the appropriate concentrations for each are selected, both the anti-IgM and the anti-IgG conjugates should develop the same color intensity as predetermined standards upon binding to the target antibody. Each conjugate then has the ability to detect the same amount of target antibody in a sample within a given time period. The concentration of the antibodies in each respective labeling reagent may differ, but the rate of binding to antibody in the receiving well has been substantially normalized.

It should also be noted that a balance of concentrations, normalizing the binding of the anti-IgG and anti-IgM labeling reagents, is critical to enable detection of situations wherein the concentration of these respective antibodies in a patients' sample are nearly equal. In the preferred embodiments, the final concentrations (once that conjugate is added to the receiving well) for each of the anti-IgM or anti-IgG antibody labeling reagent ranges from about 1.5 micrograms/ml to about 4.5 micrograms/ml preferably about 2 micrograms/ml to about 4 micrograms/ml, most preferably 2 micrograms/ml to about 3 micrograms/ml. It should be appreciated, however, that these concentrations may vary substantially if a different incubation period is chosen, or an enzyme other than horseradish peroxidase is used, or the like.

The diagnostic kit of the invention may also include a substrate for the enzyme that is linked as the indicating means to the anti-IgM and IgG conjugates. Any substrate that will allow the linked enzyme to act on it to produce a detectable result is suitable in this regard. In the preferred embodiments, wherein horseradish peroxidase is the enzyme, any substrate that will allow this enzyme to act on it will be suitable, such as conventionally used orthophenylene diamine (OPD) in stabilized hydrogen peroxide or an ABTS system. Preferred for use herein is the ABTS system in which substrate A and B are mixed prior to use, which produces a green reaction color when the enzyme works on it, as opposed to a yellow color produced by OPD. The green is visually easier to perceive then the yellow. Additionally, this substrate system is not light sensitive as is the orthophenylene diamine system.

Additional components of the diagnostic kit that are packaged and supplied in the kit or supplied by the end user are washing solutions such as saline-Tween TM, and the like, as well as components that will stop the substrate-enzyme reaction such as SDS, acid, and the like. This enables the color development to be arrested at the developed stage for facility in color comparison between the wells.

The following examples more specifically define certain embodiments of the present invention, but should not be considered limitative thereof.

EXAMPLES

In describing the use of the assay support device of the invention in the preferred immunoassay wherein a ratio of IgG and IgM antibodies is detected, we refer now to the assay device depicted in FIG. 1 for clarification. Equal aliquots of a biological sample, such as saliva, serum, whole blood, plasma, and the like, possibly containing target analyte, are added to each of the receiving wells, precoated with Epstein-Barr nuclear antigen (EBNA) Aliquots can range from about 25 microliters to about 150 microliters, preferably 40 to about 60. The assay support then rests at room temperature for an incubation period of at least about two minutes, to allow any antibodies in the biological sample to bind to the antigen coated on the device. Unbound reactants are then washed from the device by merely dipping the series into a vessel containing suitable washing solutions such as saline in combination with Tween TM 20. The series is returned to the tabletop to lay flatly, blotted gently with a paper towel or similar absorbent material. Next, to receiving well 18 is added labeling reagent, an aliquot of anti-IgM antibody, and to receiving well 20 is added an aliquot of anti-IgG antibody, the two aliquots being equal, and in amounts so as to not overflow the wells, preferably about 100 microliters. The device is allowed to rest for a period of incubation of at least about two minutes so that the conjugated labeling reagent can react with target antibody bound to the precoated antigen. A second washing step and blotting step is employed to rid the sample of target antibody that did not bind to the pre-coated protein and to each of receiving wells 18 and 20 is added an aliquot of substrate, substrate A and B (Kirkegaard & Perry) which have been mixed previously as per the manufacturer's instructions. Here again, the amount of the substrate solution added to each well is equal, so as to avoid skewing any of the reaction results. This enables the relative ratio of one antibody to the other to be ascertained. The period of incubation for this substrate step ranges from about 2 minutes to about 2½ minutes, preferably 2 minutes. If the substrate is allowed to incubate for a greater period of time with the immunoreaction product immobilized onto the concave surface of the assay support, it is possible that the results would be skewed. The IgM is a larger antibody then the IgG, thus, more of the HRP is present on it. The reaction colors may thus tend to develop at different rates. However, at some point, the rates would plateau, and it would appear for all intents and purposes that the ratio of one antibody to the other were a one to one ratio. Hence, one must compare the color development prior to reaching this plateau, on the ascending portion of a color development curve (wherein color develops as a function of time). Within the context of the preferred concentrations of anti-IgG and anti-IgM, normalized for binding affinity distinctions as described previously, it has been discovered that the 2-minute incubation period with substrate A and B provides what is referred to as a "2-minute window", where the user may compare the colors or color intensity produced in the IgG well, versus the IgM well, to get an appropriate and real relative ratio of one antibody to the other.

The reaction is then optionally stopped at this 2-minute window by the addition of a component that will deactivate the enzyme, such as SDS, acid, and the like. In this manner, the color development may be arrested at the 2-minute stage and color comparison studied.

What is claimed is:

1. An assay support, generally planar and elongated in shape, and comprising a gripping section, a sample receiving well section, and a connecting section therebetween, each of said sections being aligned along a longitudinal axis;

said sample receiving well section comprising at least two spaced-apart receiving wells; each of said wells having an open end on a first face of said support, a concave inner surface extending concavely into said support, and a convex outer surface which projects convexly from an opposed face of said support;

said convex outer surface of at least one of said wells provided with at least one stabilizing leg constructed and arranged to preclude rotation of said wells when resting on a flat surface;

said assay support provided with a leveling projection extending from said opposed face so as to cooperate with said at least one stabilizing leg to maintain said support level when resting on a flat surface;

said sample receiving section in the space between said wells comprises a dam means projecting from the first face of said support so as to preclude the flow of a liquid sample from one of said wells to another of said wells.

2. The assay support of claim 1 wherein said concave inner surface of said wells further comprises ridges, adapted to aid in the homogenous dispersing of liquid reactants deposited therein.

3. The assay support of claim 2 wherein said ridges are in the form of concentric circles.

4. The assay support of claim 1 wherein said dam means further comprises at least one labeling portion.

5. The assay support of claim 4 wherein said at least one labeling portion is contiguous with said dam means, and projects from said first face of said planar support to a height equal to that of said dam means.

6. The assay support of claim 5 wherein said at least one labeling portion is generally triangular in shape with an apex extending toward one of said receiving wells.

7. The assay support of claim 6 wherein said at least one labeling portion further comprises labeling indicia.

8. The assay support of claim 7 wherein within said connecting section of said assay support includes a labeling region for the labeling of said assay support.

9. The assay support of claim 8 wherein said labeling region is contiguous with said gripping section of said assay support.

10. The assay support of claim 9 wherein said leveling projection, adapted to cooperate with at least one stabilizing leg, is positioned between said labeling region of said connecting section and said gripping section.

11. The assay support of claim 10 wherein said gripping section comprises ridges to facilitate the manual gripping of said support.

12. The assay support of claim 11 wherein said gripping section further comprises numbering indicia.

13. A plurality of detachably connected assay supports wherein each of said assay supports is generally planar and elongated in shape and comprises a gripping section, a sample receiving well section and a connecting section therebetween, each of said sections being aligned along a longitudinal axis;

said sample receiving well section comprising at least two spaced-apart receiving wells; each of said wells having an open end on a first face of said support, a concave inner surface extending concavely into said support, and a convex outer surface which projects convexly from an opposed face of said support;

said convex surface of at least one of said wells provided with at least one stabilizing leg constructed and arranged so as to preclude rotation of said wells when resting on a flat surface;

said assay support provided with a leveling projection extending from said opposed face so as to cooperate with said at least one stabilizing leg to maintain said support level when resting on a flat surface;

said sample receiving well section in the space between said wells comprises dam means projecting from the first face of said planar support, so as to preclude the flow of a liquid sample from one of said wells to another of said wells.

14. The plurality of assay supports of claim 13 wherein said assay supports are detachably connected one to another generally at said gripping section of each of said supports.

15. The detachably connected assay supports of claim 14, wherein said supports are connected in a substantially single plane to form a planar series of said supports for applying reagents to said wells by dipping said wells into a bath together with a plurality of similar planar series, so that the first face of the assay supports of said series faces the opposing face of an adjacent planar series; said assay supports each including a spacer projection extending from the sample receiving section of the opposed face so that it will cooperate with the dam means of the assay support of an adjacent planar series of said assay supports to keep the convex surface of the wells of said planar series apart from the concave surface of the wells of the adjacent planar series of assay supports.

16. The plurality of assay supports of claim 15 wherein said plurality of assay supports comprises about 8 to about 10 of said detachably connected assay supports.

17. An assay support, useful in conducting immunoassay determinations of the ratio of IgG to IgM antibodies in biological samples, said support generally planar and elongated in shape, and comprising a gripping section, a sample receiving well section, and a connecting section therebetween, each of said sections being aligned along a longitudinal axis;

said sample receiving well section comprising two spaced-apart receiving wells; each of said wells having an open end on a first face of said support, a concave inner surface extending concavely into said support, said inner surface comprising concentric circles; and a convex outer surface which projects convexly from an opposed face of said support;

said convex outer surface of at least one of said wells includes at least one stabilizing leg adapted to preclude rotation of said wells when resting on a flat surface;

said assay support comprises a leveling projection extending from said opposed face so as to cooperate with said at least one stabilizing leg to maintain said support level when resting on a flat surface; said sample receiving well section also comprising in the space between said wells dam means projecting from the first face of said support so as to preclude the flow of a liquid sample from one of said wells to another of said wells.

said dam means further comprising a labeling portion contiguous therewith and projecting from said first face of said support to a height equal to that of the dam means; said labeling portion being generally triangular in shape with an apex extending toward one of said receiving wells.

18. The device of claim 17, wherein said receiving well section is pre-coated with a protein capable of binding to an antibody.

* * * * *